(12) United States Patent
Frings

(10) Patent No.: US 10,166,037 B2
(45) Date of Patent: Jan. 1, 2019

(54) SURGICAL TOOL, MICRO-SURGICAL INSTRUMENT AND ACTUATION METHOD FOR BOTH

(71) Applicant: Karl Storz SE & Co. KG, Tuttlingen (DE)

(72) Inventor: Hermann-Josef Frings, Aachen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 1132 days.

(21) Appl. No.: 14/265,080

(22) Filed: Apr. 29, 2014

(65) Prior Publication Data

US 2014/0324087 A1 Oct. 30, 2014

(30) Foreign Application Priority Data

Apr. 29, 2013 (DE) .......................... 10 2013 007 315

(51) Int. Cl.
| | | |
|---|---|---|
| A61B 17/29 | (2006.01) | |
| A61B 17/32 | (2006.01) | |
| A61B 17/295 | (2006.01) | |
| A61B 17/3201 | (2006.01) | |

(52) U.S. Cl.
CPC ............ *A61B 17/29* (2013.01); *A61B 17/295* (2013.01); *A61B 17/3201* (2013.01); *A61B 17/320016* (2013.01); *A61B 2017/2932* (2013.01); *A61B 2017/2948* (2013.01)

(58) Field of Classification Search
CPC ............ A61B 17/29; A61B 17/320016; A61B 17/295; A61B 17/3201

USPC ........................................ 606/170, 205, 207
See application file for complete search history.

(56) References Cited

U.S. PATENT DOCUMENTS

| | | | |
|---|---|---|---|
| 4,729,374 A | 3/1988 | Alfranca | |
| 4,848,338 A | 7/1989 | De Satnick et al. | |
| 5,454,826 A | 10/1995 | Ueda | |
| 8,241,228 B1 | 8/2012 | Cohen et al. | |
| 8,585,736 B2* | 11/2013 | Horner .................. | A61B 17/29 |
| | | | 606/207 |
| 2011/0301604 A1* | 12/2011 | Horner .................. | A61B 17/29 |
| | | | 606/52 |

FOREIGN PATENT DOCUMENTS

| | | |
|---|---|---|
| DE | 2759488 C2 | 6/1982 |
| DE | 3523022 A1 | 3/1986 |
| DE | 4136861 A1 | 5/1993 |

(Continued)

*Primary Examiner* — Vy Bui
(74) *Attorney, Agent, or Firm* — Whitmyer IP Group LLC

(57) ABSTRACT

An actuation method for a surgical tool and the tool itself, which includes a proximal coupling portion from which two hydraulically actuatable, pivotably connected members extend. Each of the branches, at least at their distal ends, have an active portion and form in the coupling portion a boundary for at least part of a fluid-tight, fluid-fillable cavity. A pivot position of the members and a volume of the fluid in the cavity are operatively coupled with one another. An actuation method for a micro-surgical tool and the micro-surgical tool, which includes a proximal handle with an actuation device and a distally disposed inventive hydraulically actuatable surgical tool, which is connected by a shaft with the handle and can be actuated by the actuation device.

17 Claims, 4 Drawing Sheets

(56) References Cited

FOREIGN PATENT DOCUMENTS

| | | | |
|---|---|---|---|
| DE | 19537897 | A1 | 3/1997 |
| DE | 202007009310 | U1 | 8/2007 |
| EP | 2392270 | A1 | 12/2011 |
| GB | 2161707 | A | 1/1986 |
| JP | 2006141652 | A | 6/2006 |

\* cited by examiner

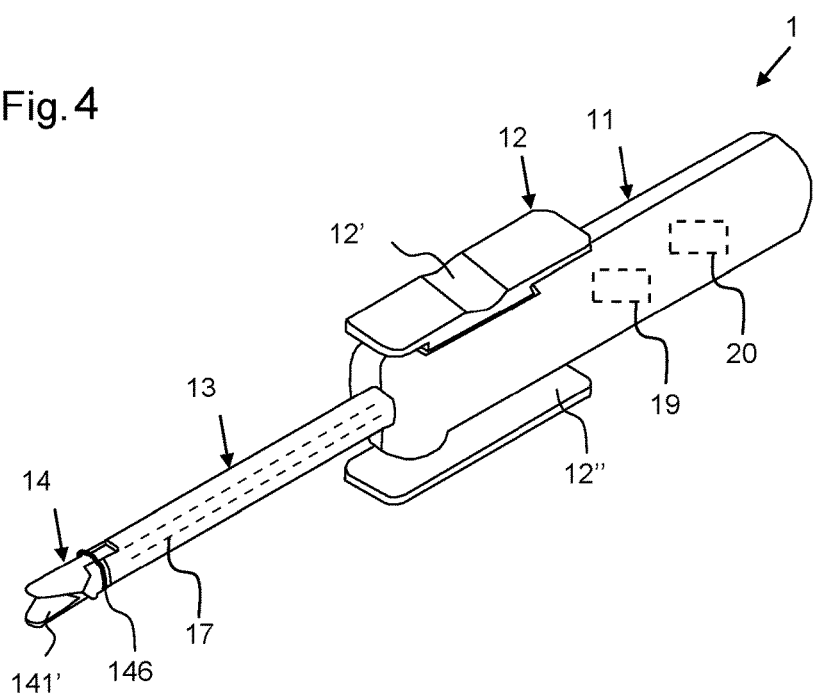

SURGICAL TOOL, MICRO-SURGICAL INSTRUMENT AND ACTUATION METHOD FOR BOTH

FIELD OF THE INVENTION

The following invention relates to a surgical tool and a micro-surgical instrument as well as an actuation method for both.

BACKGROUND OF THE INVENTION

In minimally invasive surgery, surgical tools and micro-surgical instruments are used in which the operator sees only a two-dimensional image of the surgical site and is therefore particularly dependent on his sense of touch. However, he cannot feel the tissue in the surgical area directly, but only indirectly, and therefore has to rely on endoscopes or laparoscopes that incorporate the surgical tool at the end of a shaft. It is possible in this context to use grippers, forceps or scissors with movable members as surgical tools.

To avoid damaging tissue as a result of excessive force impact, such instruments can provide the operator with feedback via the force being applied (force feedback). Such instruments are essentially operated purely mechanically; that is, the force that the operator exerts on the actuation device is conducted via Bowden cables or push rods to the surgical tool via the shaft. Gearboxes are often provided on the tool and/or on the handle for force or torque conversion. As a rule, however, these gearboxes do not have a linear transmission ratio, and consequently the operator grips tissues of varying thickness with a different force, even when the actuation force is the same. In addition, friction losses, which occur in the gearbox and especially on the diverted paths of Bowden cables, make the instrument sluggish, sometimes causing tasks to be fatiguing.

Therefore micro-surgical instruments have been developed with hydraulic actuation that comprise lower losses in force transmission from the actuation device to the tool than those with mechanical transmission.

Thus patent DE 195 37 897 A1, for instance, describes an endoscopic instrument on whose distal end of a shaft various surgical tools are disposed. Here the individual surgical tools can be brought into an operating position by a hydraulic actuator, whereas the others remain in resting position. However, the hydraulic actuator, such as a piston-cylinder arrangement, does not actuate the surgical tool directly but only moves it into the operating position. Therefore many lines must be fed through the shaft, unnecessarily increasing the structural size of the instrument.

In addition, patent DE 41 36 861 C2 discloses a micro-surgical instrument that includes a surgical tool that is pivotably disposed at the distal end of the shaft. The surgical tool can be operated by means of a handgrip, such that the force or signal transmission for operating the surgical tool occurs via control cables electrically, hydraulically or pneumatically. Hydraulic actuation of the surgical tool is not described there in any further detail.

In addition, patent DE 27 59 488 C2 describes a surgical instrument with hydraulically actuated tool of the same structural type, in which the tool is actuated by a hydraulic cylinder whose piston is coupled with a relay lever, which in turn acts on the members of the tool. The hydraulic cylinder can be impacted with pressure by means of a pressure-generating cylinder in the handgrip. The instrument disclosed in the patent comprises a number of parts, which are produced with some complexity and expense, and because of the many hydraulic connections and displaced cylinder linings, there is a constant risk of leakages Finally, patent DE 35 23 022 A1 also discloses a surgical instrument of known structural type, in which a scissors is hinged at the outermost point of the shaft, so that it can open contrary to the insertion direction of the shaft. The scissors is actuated by sliding the shaft interior opposite to the shaft exterior by means of the handgrip. Actuation can also occur hydraulically, but this option is not described in any detail.

SUMMARY OF THE INVENTION

On the basis of this summary of the prior art, it is the object of the present invention to provide an improved surgical tool, which makes possible a linear feedback of the actuation force over the greatest possible actuation range and is composed of few individual components, which can be produced at reasonable cost.

This object is fulfilled by a surgical tool having a proximal coupling portion from which two hydraulically actuatable, pivotably connected members extend, each having an active portion, at least at their distal ends, characterized in that the members in the coupling portion form a boundary for at least a part of a fluid-tight, fluid-fillable cavity, such that a pivot position of the members and a volume of the fluid are operatively coupled together in the cavity.

The invention has the additional object of making it possible to actuate such instruments with improved feedback. This object is achieved with a method including the steps filling the cavity with a predetermined fluid volume, thereby increasing the volume of the cavity and moving the firmly coupled members all the way to a predetermined pivot position, and/or adjusting a predetermined pressure in the cavity, thereby transmitting a pressure force from the cavity to the members and exert a predetermined actuation force of the members.

An additional object is to provide an improved micro-surgical instrument that allows an operator improved force feedback and non-fatiguing tasks.

This object is achieved by means of a micro-surgical instrument having a proximal handle with an actuation device and comprising a distal hydraulically actuatable surgical tool, which is connected by a shaft with the handle, wherein the surgical tool is a surgical tool according to at least one of the claims and the pressure and filling of the cavity of the surgical tool are adjustable by means of the actuation device. In addition, a method for a micro-surgical instrument according to claims, including the steps actuating the actuation device with at least a predetermined actuation force, from the predetermined actuation force, according to a predetermined transmission ratio, determining and adjusting the pressure of the cavity of the surgical tool, thereby transmitting a pressure force from the cavity to the members and exerting a predetermined actuation force of the members, fulfills the object of making possible a correspondingly improved operation of such instruments.

Preferred embodiments of the apparatuses and/or the methods are described in each case by the dependent claims.

The inventive surgical tool, according to a first embodiment, comprises a proximal coupling portion from which there extend two hydraulically actuatable, pivotably connected members. Said members each have at least one working portion at their distal ends, and in the coupling portion constitute a boundary for at least part of a fluid-tight and fluid-fillable cavity. The pivotal position of the members and the fluid volume in the cavity are operatively coupled with one another.

The terms "proximal" and "distal" in this document are to be understood in reference to the affixing of the surgical tool on a tool shaft, as in generic surgical tools in the manner known in the prior art. Accordingly, the surgical tool is distally affixed and can be operated with a proximal handle.

The fluid capacity in the cavity and the pivoting position of the members are mutually dependent according to previously known and determinable relations, whereas the pivoting position of the members can be determined simply by adjusting the filling and the pressure in the cavity. The force transmission from the fluid in the cavity to the members occurs directly by pressure impact on the members, without requiring hydraulic cylinders, relay levers or other gear works, because in a fluid the pressure forces always act equally in all spatial directions. Except for pressure loss of the fluid on flowing info the cavity, scarcely any frictional losses occur.

The inventive surgical tool can therefore be used with markedly lesser operating forces than known surgical tools of this type, and it also makes possible a decidedly better force feedback than tools that, for instance, are operated by toggle levers.

Advantageously, the inventive surgical tool is constructed only from a small number of parts, so that it can be produced very economically. The members surround the fluid-filled cavity directly, while an insulating surface coating or other contact seals can be applied to the insulating surfaces of the members in order to ensure that the cavity is fluid-tight. However, such insulating elements have no essential influence on the flow of forces and are intended merely to prevent leaks that must be avoided at all costs for use in the human body. Advantageously, however, a biologically harmless and/or sterile fluid can be employed, so that any leaking in the hydraulic circuit does not lead to an infection or contamination of surrounding tissue.

In an additional embodiment, the surgical tool can comprise in the coupling portion a tool housing with at least one recess, in said recess the pivotably connected members are fed in the recess with a guide portion, such that the tool housing with the members constitutes the cavity. In addition, a hydraulic connection, fluidically linked to the cavity, can be affixed on the tool housing.

in this embodiment the cavity is bounded both above and below by the guide portion of a member and on the lateral as well as proximal and distal boundary surfaces by the fool housing. Above and below are the spatial directions predetermined by the opening or closing direction of the members. The guide portion here is advantageously contiguous with an end facing away from the active portion of the members. Because a relative movement occurs between the members and the tool housing when the members are moved, they must be insulated from one another. This can be achieved, for example, by a coating on the surface of the tool housing facing the inside of the cavity or, for instance, by means of an G-ring situated inside a recessed groove of the mantle surface of the guide portions. To achieve durable insulation, the guide portions should comprise rounded edges along the recessed groove.

In yet another embodiment, the members can be mounted pivotably in the tool housing on a guide axis and the recess can be situated in the pivot plane of the members.

The guide axis can extend advantageously between the guide portion and the active portion of the members, so that a force exerted on the guide portion generates torque around the guide axis, resulting in actuation of the members. Advantageously, thanks to the orientation of the recess parallel to the pivot plane of the members, on the guide portions only those forces engage that are active in the pivot plane of the members, whereas the inner wall of the tool housing absorbs the forces that act parallel to the pivot axis of the members.

In addition, the hydraulic connection can lead into a balloon situated in the cavity. It is advantageous if the balloon is connected to the members and especially advantageous if it is cemented to the members, at least at selective points.

To facilitate insulation, the cavity is configured with the balloon, a kind of "bubble," which clings to the boundary walls of the cavity when filled up. in this case it is possible to dispense, for example, with insulating provisions between the guide portions of the members and the tool housing; it is necessary merely to maintain a maximum gap space, because otherwise the balloon could slide into the gap when pressure is applied. According to this embodiment it is possible to produce the surgical tool even more economically because much lower tolerances need to be met. By cementing the balloon with the guide portions, it is possible not only to exert pressure forces on the members, but also tractive forces upon emptying or shrinking the balloon, so that additional return motion devices can be dispensed with. However, the balloon's wall strength should not be too great, because otherwise the force necessary for extending it becomes too great, and thus the force feedback properties can be adversely affected because the balloon's return force continually acts on the fluid, unless an actuation device for exerting pressure on the balloon is pre-tensed with the same force as the balloon, so that the respective return forces would exactly offset one another.

Alternatively, an electrical control element for adjusting pressure and filling of the cavity can be fluidically connected with the cavity. Advantageously, said control element should be a pump, which is connected with the hydraulic connection, The pump, in addition, can be disposed on the tool housing and can advantageously be fluidically connected with an expansion reservoir, which can also be disposed on the tool housing.

Miniaturized pumps, for example membrane pumps the size of match stick heads, are known in the art, so that this embodiment increases the total structural size of the inventive surgical fool only insignificantly.

According to an additional embodiment, the surgical tool can comprise a return device with which the members can be returned to their resting position. Said return device can be advantageously a spring lock ring or an elastomer ring, which especially advantageously is conductively connected with the guide portion of the members. In resting position, the members are advantageously open.

To restore the members' position, the return device can exert pressure or tractive forces; that is, it can either "press" the members from inside into the resting position or can pull them from outside, if the return device happens to be a spring lock or elastomer ring set from outside onto the guide portions of the members, then it is advantageous if it engages in an outlying recess groove of the guide portions so that it does not slide downward accidentally, in selecting the spring lock ring, however, care must be taken that the exerted return force is just sufficient to overcome the friction of the pivotable linkage and the loss of pressure in the fluid streaming out of the cavity, since otherwise the force feedback properties can be negatively affected by this as well. This can be prevented, however, if the actuation device, for example a handgrip, is additionally pre-tensed by the amount of the return force of the spring lock ring, so that the two forces cancel one another and a very sensitive force feedback becomes possible.

To prevent tissue from being damaged by excessive force impact, the micro-surgical instrument can also comprise a relief valve that opens with a predetermined triggering pressure and is connected, for example, to a return pipe. The return pipe can be dispensed with, however, if the hydraulic fluid happens to be a bio-compatible fluid.

In their active portions, the members in another embodiment can comprise blades or gripping surfaces. AH types of known gripping surfaces can be used here, in particular needle gripping devices or atraumatically designed gripping surfaces suitable for grasping sensitive tissue.

The actuation method for the inventive surgical tool includes the following steps:
  fill the cavity with a predetermined fluid volume, thereby increase the volume of the cavity and move the firmly coupled members ail the way to a predetermined pivot position, and/or
  adjust a predetermined pressure in the cavity, thereby transmit a pressure force from the cavity to the members, and exert a predetermined actuation force of the members.

A compressible or non-compressible fluid can be used here. If a non-compressible fluid is selected, then no movement of the members can occur without modifying the fluid volume of the cavity; the modification of the fluid quantity depends only on the kinematics and geometry of the members or of the cavity. If, on the other hand, a compressible fluid is to be used: In this case, the fluid volume that is to be added to or taken from the cavity to modify the pivot position also depends on the forces on the members and thus on the pressure in the cavity. As a rule, however, a non-compressible fluid is used because it allows a better force transmission, and leaks in the hydraulic system do not lead to any sudden expansion of the fluid.

A first embodiment of the micro-surgical instrument comprises a proximal handle with an actuation device and a distally disposed inventive, hydraulically actuatable surgical tool. The surgical tool is connected with the handle through a shaft, while the pressure and the filling of the cavity of the surgical tool can be adjusted by means of the actuation device.

The handle or the combination of handle and actuation device can be, for example, a pincer grip, a forceps grip, a pistol grip or a ring control system. The coupling for transmitting the actuation parameters to the surgical tool can be performed mechanically, hydraulically, electrically or even optically. The transmission ratio between the actuation device and the movement of the members of the surgical tool can be constant or adjustable, so that the adjustability of the transmission ratio meets requirements during an operation, in an operation there must frequently be alternations between activities that require various sensitivity, for example gripping, dissecting and/or severing various tissue types and holding a needle, so that each of these activities requires different operating forces of the surgical tool.

In an additional embodiment of the micro-surgical instrument, the surgical tool can be connected with the shaft permanently or intermittently. The handle can advantageously comprise a return apparatus for restoring the actuation device to the resting position.

Return devices here can be taken to mean springed components that, when activated, exert a return force on the operating device or else an operating device comprising operating surfaces for bidirectional operation, for example similarly to the handle of a scissors, so that an operator can actively both close and open the surgical instrument.

According to another embodiment, there can be positioned on the handle a pressure-generating device that can be actuated with the actuating device. The pressure-generating device is fluidically connected by a fluid feeder device, such as a tube or hose, with the cavity of the surgical tool, preferably with the hydraulic connection. In addition, the pressure-generating device can advantageously be a fluid-filled balloon that can be compressed with the actuating device.

The balloon and the cavity thus form a closed hydraulic system; that is, if the balloon of the pressure-generating device is pressed together, fluid is pumped out of the balloon into the cavity, so that its volume increases and the members of the surgical tool are actuated. Use of a balloon is a very economical solution, clearly more so than a hydraulic master cylinder. The diameter of the fluid feeder device may not be selected too small and/or the roughness not too great, because otherwise a greater pressure loss occurs in the fluid feeder device because of increased streaming speed, making it difficult again to precisely operate the micro-surgical instrument and possibly distorting force feedback during a movement of the surgical tool.

Alternatively, there can be disposed on the handle at least one electrical measuring element with which at least the actuation force of the actuation device can be measured. Advantageously, in addition to the actuation force, the actuation path is also measurable. The electrical measuring element is operatively linked with the electrical control element of the surgical tool.

In this embodiment, no hydraulic lines are necessary through the shaft, so that the shaft can be constructed with a smaller diameter. The measuring element is connected directly or indirectly with the control element of the surgical tool. Measuring elements for measuring force and/or pathway are known in the art and also available in miniaturized construction. The measured actuation parameters, such as pathway and/or force, can be converted to adjust the transmission ratio by appropriate interposed electrical or electronic switches. It is also conceivable that a microprocessor as well as a storage device are interposed in order to allow call-up of predetermined transmission profiles by means of an operational apparatus. To allow force feedback, servo-motors can also be disposed on the handle that act on the actuation device proportionately to the actuation force of the members.

According to another embodiment, a push rod that is longitudinally axially slidable can be disposed in the shaft and is mechanically coupled with the actuation device and extends ail the way to the surgical tool. The push rod dips into the cavity upon actuation of the actuation device along a longitudinal portion.

Actuation of the surgical tool here remains hydraulic, whereas the signal or force transmission to trigger the hydraulic actuation mechanism occurs mechanically. Because the push rod dips into the cavity, the fluid is forced into the only possible expansion direction and the members move. The push rod constitutes almost an actuation piston in its end portion that dips into the cavity. The insulation is not critical and can be provided by contact insulations or any additional insulation can be dispensed with if the cavity is lined with the balloon.

In addition, the shaft can be pliable and/or rigid at least along a longitudinal portion. In addition or as an alternative, the shaft can be adjustable lengthwise, and a telescopable shaft is advantageous. The shaft can also comprise at least one joint, such that a joint with two rotational degrees of freedom is preferred.

The type of shaft can be selected according to the requirements of the type of operation. Corresponding to the typical structure of laparoscopic instruments, it can be completely rigid and would consist for simplicity's sake of a single tube, in which either a hose can be inserted or which itself can constitute the fluid feeder device. Alternatively if is also possible to provide that a shaft that is basically rigid in its own right comprises pivotal joints at certain locations. A hose can even be fed without problem through a jointed portion, whereas with known mechanical solutions one expensive, delicate and friction-prone transmission joint of the push rod would be necessary for each joint. It is even possible to move individual joints controllably by regulators, so that the orientation of the surgical tool at the distal end of the shaft can be controlled, for example, by an operating device on the handle. A flexible shaft can take the form, for instance, of a swan's neck structure and, in combination with the hydraulic or electrical operation, can offer particular advantages: Contrary to known systems actuated by Bowden cables, no modification in the actuation characteristic can be determined, in particular with a tightly curved shaft.

A first embodiment of the actuation method for an inventive micro-surgical instrument includes the following steps:
actuate the actuation device with at least a predetermined actuation force,
from the predetermined actuation force, according to a predetermined transmission ratio, determine and adjust the pressure of the cavity of the surgical tool,
thereby transmit a pressure force from the cavity to the members and exert a predetermined actuation force of the members.

The members of the surgical tool in this case are not moved or are not moved significantly, which requires that a rigid body, for example a needle, is disposed between the members.

According to an additional embodiment of the actuation method, the actuation device can be actuated with a predetermined actuation force and a predetermined actuation pathway. Then the method includes the additional steps:
from the predetermined actuation pathway, according to the predetermined transmission ratio, determine and adjust the filling of the cavity of the surgical tool,
thereby move the firmly coupled members ail the way to a predetermined pivot position.

The predetermined transmission ratio for the force and/or pathway transmission can be achieved by adjusting the kinematics of the surgical tool, of the surfaces on which the fluid pressure acts, and/or of the kinematics of the actuation device. With electrical or electronic signal transmission, such an adjustment can be made even more easily without requiring modifications to mechanical and/or hydraulic systems.

These and other advantages are discussed in the following description with reference to the accompanying drawings. Reference to the drawings serves to support the description and facilitate understanding of the subjects. Objects or parts of objects that are essentially identical or similar can be labeled with the same reference numbers. The drawings are merely schematic depictions of embodiments of the invention, as follows.

BRIEF DESCRIPTION OF THE DRAWINGS

FIG. 4 shows a perspective view of the micro-surgical instrument.

DETAILED DESCRIPTION OF THE INVENTION

Figure 1A:
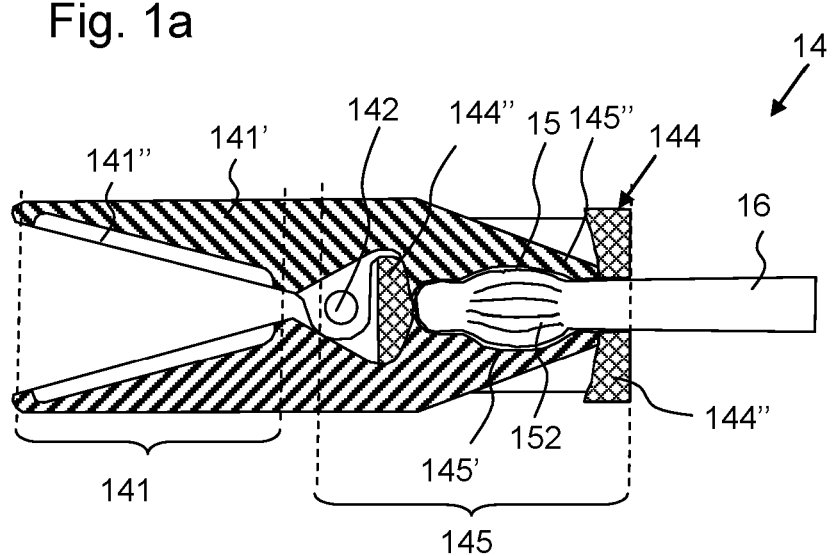
FIG. 1a shows a sectional view of the surgical tool with members opened.

Depicted in FIG. 1a is a longitudinal section of the surgical tool 14 through the center plane. It comprises two panels 141' that are pivotally disposed on a guide axis 142, such that the guide axis 142 is disposed in a tool housing 144. With the coupling portion 145, more precisely with the outer surfaces of the tool housing 144, the surgical tool 14 can be coupled with a shaft of a micro-surgical instrument in order to be used in minimally invasive surgery. The members 141' bear gripping surfaces 141" in their active portion 141, such that it is also possible, although not illustrated, that other active surfaces, such as blades for instance, are present in the active portion 141. At the other end of the members 141', which faces away from the active portion 141, the guide portion 145", the members 141' surround a fluid-filled cavity 15, whose volume changes depending on the pivot position of the members 141'. The guide portions 145" are arranged in a recess 144' (see FIG. 2b) of the tool housing 144, so that the cavity 15 is bounded both above and below by the guide portions 145" and laterally by the wails of the recess 144' (see FIG. 2b).

For better insulation, the cavity 15 is lined with a balloon 152, which is fluidically connected with a fluid feeder device 18. An embodiment without the balloon 152 is also possible; however, the requirements in terms of dimensional stability and surface qualify of the insulating surfaces 148,144" (see also FIG. 2a) are very high in this case; the slightest wear on the insulating surfaces 148, 144" could result in leaks, which must be excluded in using the surgical tool 14 in the human body. The balloon's 152 wall thickness, however, may not be too great, because otherwise its return force upon filling would be excessive. In this case accurate feedback of the actuation force would not be possible, because pressure in the cavity 15 would be determined decisively by the return force of the balloon 152. Therefore the wall thickness of the balloon 152 should be selected as precisely adequate to withstand the maximum occurring operating pressure and sufficiently robust against mechanical damage. To prevent damage to the balloon 152, the edges of the recesses 145' of the members 141' that partly make up the cavity 15 are also rounded. To allow the members 141' to be opened as widely as possible, the recesses 145' are great enough that the empty balloon 152 can be completely absorbed in them.

The cavity 15 or the balloon 152 can be filled with or drained of fluid by the fluid feeder device 16. If the content is increased, the balloon 152 first becomes contiguous with the recesses 145' of the members 141, and then the members 141' close as the result of force exerted by the balloon 152 on the guide portions 145", members 141' and the resulting torque around the rotary point of the guide axis 142.

Figure 1B:
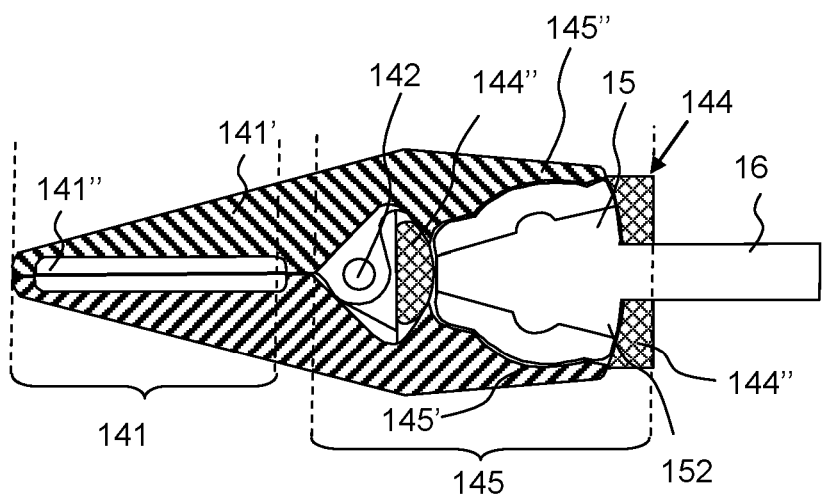
FIG. 1b shows a sectional view of the surgical tool with members closed.

The position with closed members 141' and filled balloon 152 is depicted in the sectional view in FIG. 1b. The balloon 152 presses here completely against the surfaces of the recesses 145'. The contours of the recesses 145' in the sectional plane take the shape of the balloon 152, because the recesses 145' comprise a variable cross-section that is normal to the plane of movement of the members 141'. in the filling of the balloon 152, it can expand upward/downward only in the respective pivot direction of the members 141, whereas its expansion to the proximal and distal ends is prevented by boundary portions 144" of the tool housing 144. Upon filling and/or pressure modification of the balloon 152, force is exerted directly on the members 141', without requiring the force to be diverted by additional bell cranks or the like.

Owing to this structure, the inventive surgical tool 14 is distinguished by having markedly fewer parts than known surgical tools with hydraulic operation, because it becomes possible to dispense with hydraulic cylinders and/or other force conversion devices. Consequently, the surgical tool 14 is comparatively economical to produce. Another cost-saving production factor is the coating of the cavity 15 with the balloon 152, since markedly lower requirements are set for dimensional stability and/or surface quality of the insulating surfaces 148, 144" than with an embodiment without balloon 152. In addition far lower operating forces are required for operation, because no friction occurs in gears and/or joints such as occur with known mechanical surgical tools.

Figure 2A:
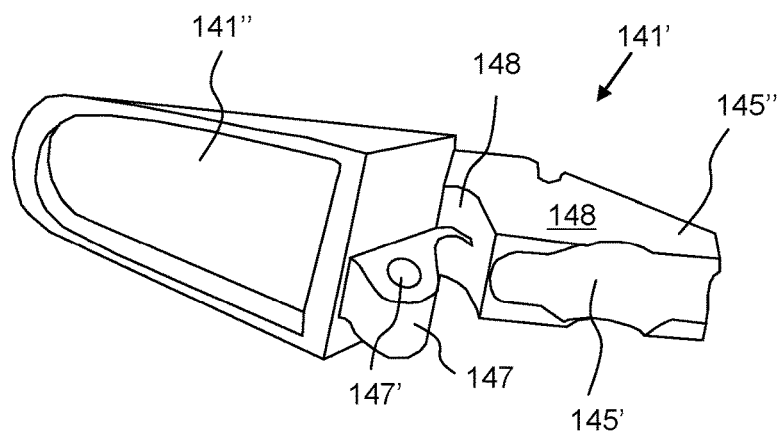
FIG. 2a shows a perspective view of a member of the surgical tool.

FIG. 2a depicts a member of the surgical tool 14 in perspective view, such that the rounded shape of the recess 145' can be clearly recognized in the member 141' that partly makes up the cavity 15 (see FIG. 1a). The recess 145' is shaped in such a way that the empty balloon 152 (see FIG. 1b) can be absorbed into it when the members 141' are opened. The member 141' comprises a hinge portion 147 in which a pass-through hole 147' is present, through which the guide axis 142 (see FIG. 2b) is inserted. The proximal area "to the right" of the hinge portion 147 is the guide portion 145" of the member 141', which is shaped in such a way that it can be fed in the recess 144' of the tool housing 144 (see FIG. 2b) in such a way that the insulating surfaces 148 and the recess 144' of the tool housing 144 either directly allow fluid-fight insulation of the cavity 15 or release only a narrow gap, so that the balloon 152 (see FIG. 1b) cannot be pressed into the gap. In addition, the gripping surface 141" of the member 141' is shown, with which swabs, needles and/or tissue can be grasped, for example.

Figure 2B:
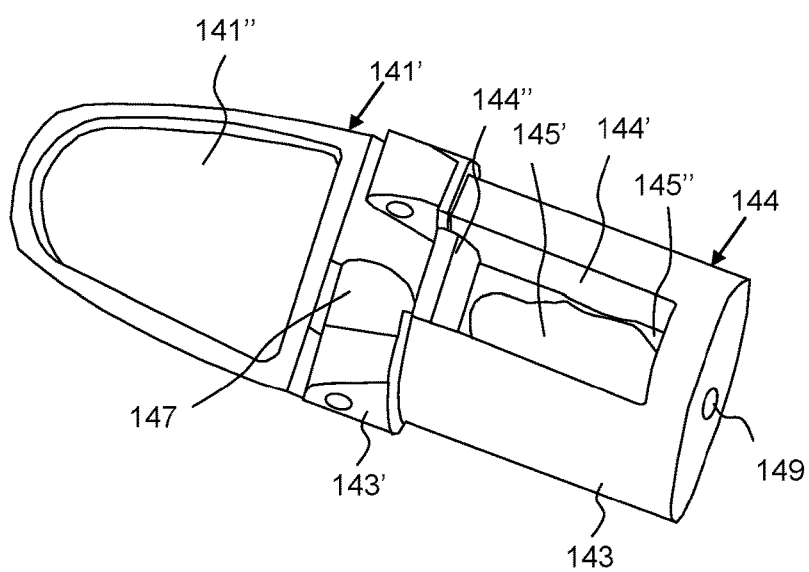
FIG. 2b shows a perspective view of a member and of the tool housing of the surgical tool.

FIG. 2b shows the tool housing 144 and the other member 141' of the surgical tool 14 (see FIG. 3), such that the other member 141' also comprises a hinge portion 147 with a pass-through hole for the guide axis 142. To assemble the surgical tool 14, the guide axis 142 (see FIG. 1a) is inserted through the pass-through holes of the respective hinge portions 147 of the members 141' as well as through the linkage portion 143' of the tool housing 144. The recess 144' comprises, in addition to two lateral wails, proximal and distal boundary portions 144", which make possible the insulation of the cavity in pairing with the insulating surfaces 148 of the guide portions 145" of the members 141'. To improve insulation of the cavity, the walls and/or the boundary portions 144" of the recess 144' can be coated with a synthetic layer or the cavity can be lined with a balloon 152 (see FIG. 3). A hydraulic connection 149, which is present on the front surface of the tool housing 144, is fluidically connected with the cavity. If a balloon 152 is used, then it is advantageous for assembling the surgical tool if the balloon can be pushed into the cavity through the hydraulic connection 149 in empty condition.

Figure 3:
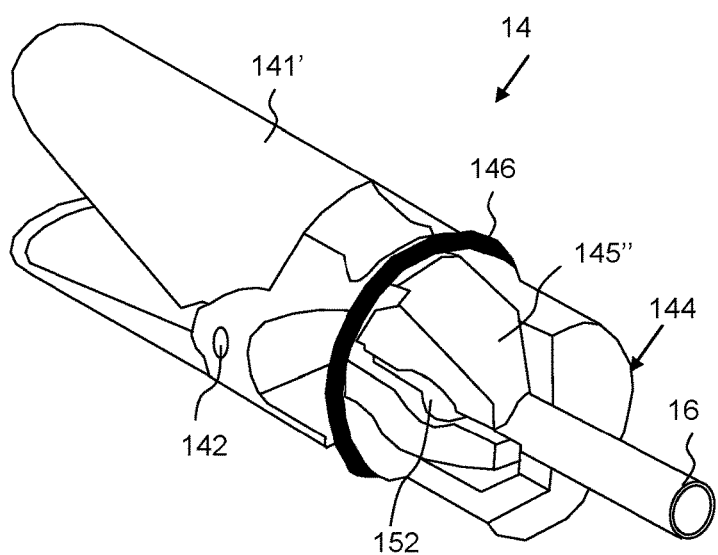
FIG. 3 shows a perspective view of the surgical tool with return device.

The perspective view of the assembled surgical tool 14 in FIG. 3 shows, in addition, a return device 146, which is disposed surrounding the tool housing 144 and the members 141'. The return device 146 here is a spring lock ring or elastomer ring that is untensed, with the members 141' in the illustrated opened position, if the members 141' are closed at their distal end, the ring of the return device 146 exerts a return force on the proximal guide portion 145" of the members. The ring of the return device 146 is inserted in corresponding recessed grooves of the members 141', so that it cannot slide down accidentally. In this illustration it can be seen clearly that the balloon 152, which here is empty, is absorbed in the cavity between the guide portions 145 of the two members 141'. The balloon 152 is fluidically connected with a tube or hose 16, by which the balloon 152 can be filled/emptied and/or impacted with pressure, in addition, over the tool housing 144 and a proximal longitudinal section of the members 141, a cover can be pushed, which covers up the return device 146 and prevents impurities from penetrating, and is not shown in the drawing. The spring stiffness of the ring of the return device 146 here should be set high enough so that the return force, with members 141 closed, is exactly sufficient to open the members 141, but it may not be too high, since otherwise the force feedback to the operator would be distorted.

FIG. 4 shows the inventive micro-surgical tool 1, which comprises a handle 11 and a surgical tool 14, with two pivotable members 141', which is connected by a shaft 13. Optionally shaft 13 may contain push rod 17. Disposed on the handle 11 is an actuation device 12, with which the surgical tool 12 can be operated. Inside the handle 11 there is a second balloon 19, which serves as pressure-generating device. Said second balloon 19 is fluidically connected in a closed hydraulic circuit with the balloon in the cavity of the surgical tool 14 and, when the actuation device 12 is actuated, is pressed together. To hydraulically connect the two balloons, a tube or hose 18 (see FIG. 3) is fed in the shaft 13, and is ideally very resistant to pressure in order to prevent force feedback from being impeded by lateral straining of the hose 16. A hose surrounded with tissue, for instance, can be used here. In an embodiment the handle 11 may comprise electronic measuring device 20.

It is also possible to provide that two hoses are fed in the shaft 13; one hose 16 for pressure supply and another for the return of fluid, which has emerged at a relief valve on the micro-surgical tool and must be fed back into a reservoir. Alternatively, the relief valve can also be disposed on the handle; thus the return hose can be dispensed with, although this is not shown in the drawings.

The actuation device 12 consists of two movable plates 12", which are pivotably attached on the inside of the handle 11; thus it forms something of a pincer grip, which can be operated with the tips of the thumb and index finger. The plates 12" each comprise a trough-shaped recess 12', which first serves ergonometric principles because the fingertips can be placed on if comfortably, and which secondly marks the position on the plates 12" at which the actuation pathway and the actuation force of the actuation device correspond precisely to the pathway and force on the members 141'. For this purpose the plates 12" of the actuation device can each comprise a pad on the inside that presses against the actuation balloon; the force insertion from the plates 12" into the balloon thus always occurs at the same position, regardless of the longitudinal position of the plates 12" at which the operator has positioned his fingertips. However, with a modification of the longitudinal-axis force insertion position on the plates, a modification of the transmission ratio can be achieved; because the plates 12" are pivotably attached, "pressing down" on the plates 12" leads by a fixed actuation pathway, depending on the force insertion position, to a different pathway of the members. An operator can deliberately make use of this "leverage characteristic" and, for holding needles for instance, in case of a large actuation pathway and a small actuation force, can select a force insertion position that allows him considerable force and a short pathway of the members. At any time, by pushing his fingertips, the operator can return to the "balanced" transmission ratio that allows him direct feedback of the force at the members, simply by feeling out the trough-shaped recess 12'.

On the handle 11 it is possible, in addition, to dispose a blocking device with which the actuation parameters of the actuation device 12 can be blocked, although this is not shown in the illustrations. This can take the form, for instance, of a slider, which is connected with the handle 11 and on whose end a catch lock is disposed. To block the pivotal position the catch lock can engage with a discrete catch relief of the actuation device 12. Alternatively, the blocking device can also block the actuation device 12 in force-fitted manner, allowing a seamless blocking.

To return the surgical tool 14 from closed to opened position, a spring lock ring 146, as shown in FIG. 3, is disposed in conductive connection surrounding the members 141'.

However, an embodiment without separate return device 146 on the surgical tool is also conceivable, but it is not shown in FIG. 4. The balloon in the cavity of the surgical tool 14 can not only close the members upon pressure impact, but can also open them again in that the balloon actively takes the guide portions of the members 141 with it upon contraction; to do so, however, the balloon would have to be connected, for instance cemented, with the guide portions of the members 141 at least at selective points.

What is claimed is:

1. A surgical tool, comprising:
a proximal coupling portion from which two hydraulically actuatable, pivotally connected members extend, each pivotally connected member having an active portion and a guide portion;
wherein the pivotally connected members form a boundary for at least a part of a fluid-tight, fluid-fillable cavity, such that a pivot position of the pivotally connected members is adjustable via a change in a volume of a fluid in the fluid-fillable cavity;
wherein the coupling portion comprises a tool housing which houses the guide portions of the pivotally connected members in a recess of the tool housing; and
wherein a hydraulic connection is disposed in the tool housing such that the tool housing and the pivotally connected members form the fluid-fillable cavity said fluid-fillable cavity is fluidically connected with the hydraulic connection.

2. The tool according to claim 1, wherein the pivotally connected members in the tool housing are pivotally disposed on at least one of a guide axis or the recess is situated in a pivot plane of the pivotally connected members.

3. The tool according to claim 1, wherein the hydraulic connection leads into a balloon, which is disposed in the cavity and cemented with the pivotally connected members, at least at selective points.

4. The tool according to claim 1, wherein the surgical tool comprises a return device, by means of which the pivotally connected members can be restored to a resting position, such that the return device is a spring lock ring or an elastomer ring, which is conductively connected with the guide portion of the pivotally connected members.

5. The tool according to claim 1, wherein the pivotally connected members in the active portion comprise blades or gripping surfaces.

6. An actuation method for a surgical tool according to claim 1, including the steps:
fill the cavity with a predetermined fluid volume, thereby increase the volume of the cavity and move the firmly coupled members all the way to a predetermined pivot position, and/or
adjust a predetermined pressure in the cavity, thereby transmit a pressure force from the cavity to the members and exert a predetermined actuation force of the members.

7. A micro-surgical instrument, comprising a proximal handle with an actuation device and comprising the surgical tool of claim 1, which is connected by a shaft with the handle, wherein a pressure and filling of the cavity of the surgical tool are adjustable by means of the actuation device.

8. The instrument according to claim 7, wherein the surgical tool is connected permanently or intermittently with the shaft.

9. The instrument according to claim 8 whereby the handle comprises a return device to restore the actuation device to a resting position.

10. The instrument according to claim 7, comprising a pressure-generating device, disposed in the handle, which can be actuated by means of the actuation device and which, by means of a fluid feeder device that is a tube or hose, is fluidically connected with the cavity of the surgical tool, with the hydraulic connection, such that the pressure-generating device is a fluid-filled balloon, which can be compressed by means of the actuation device.

11. The instrument according to claim 7, wherein the shaft is pliable or rigid at least along a longitudinal portion.

12. An actuation method for a micro-surgical instrument according to claim 7, including the steps:
actuate the actuation device with at least a predetermined actuation force,
from the predetermined actuation force, according to a predetermined transmission ratio, determine and adjust the pressure of the cavity of the surgical tool,
thereby transmit a pressure force from the cavity to the members and exert a predetermined actuation force of the members.

13. The actuation method according to claim 7, wherein the actuation device is actuated with a predetermined actuation force and a predetermined actuation pathway, including the steps:
from the predetermined actuation pathway, according to the predetermined transmission ratio, determine and adjust the filling of the cavity of the surgical tool,
thereby move the firmly coupled members as far as a predetermined pivot position.

14. The instrument according to claim 7 whereby the handle comprises a return device to restore the actuation device to a resting position.

15. The instrument according to claim 7 wherein the shaft is of adjustable length.

16. The instrument according to claim 7 wherein the shaft comprises at least one joint with two rotational degrees of freedom.

17. A surgical tool comprising:
two hydraulically actuatable members configured to be pivotable around a pivot axis;
a guide portion on each proximal end of the hydraulically actuatable members and an active portion on each distal end of the hydraulically actuatable members;

a housing comprising a housing recess;
wherein the guide portions of the hydraulically actuatable members are disposed within the housing recess and form a fluid-filled cavity within the housing recess;
wherein guide portion recesses in the guide portions form part of a boundary of the fluid-filled cavity between the guide portions; and
wherein a change in a volume of a fluid in the cavity causes a change in a pivot position of the hydraulically actuatable members.

* * * * *